US010631844B2

(12) United States Patent
Astorino et al.

(10) Patent No.: US 10,631,844 B2
(45) Date of Patent: *Apr. 28, 2020

(54) TISSUE REPAIR

(71) Applicant: Smith & Nephew, Inc., Memphis, TN (US)

(72) Inventors: Steven William Astorino, Norfolk, MA (US); Peter Klindt Sorensen, Salem, MA (US); Laura Lindsey Mills, Brighton, MA (US)

(73) Assignee: Smith & Nephew, Inc., Waltham, MA (US)

( * ) Notice: Subject to any disclaimer, the term of this patent is extended or adjusted under 35 U.S.C. 154(b) by 102 days.

This patent is subject to a terminal disclaimer.

(21) Appl. No.: 15/095,225

(22) Filed: Apr. 11, 2016

(65) Prior Publication Data
US 2016/0220243 A1 Aug. 4, 2016

Related U.S. Application Data

(60) Continuation of application No. 14/693,322, filed on Apr. 22, 2015, now Pat. No. 9,370,352, which is a
(Continued)

(51) Int. Cl.
A61B 17/04 (2006.01)
A61B 17/06 (2006.01)
A61B 17/00 (2006.01)

(52) U.S. Cl.
CPC ...... A61B 17/0401 (2013.01); A61B 17/0057 (2013.01); A61B 17/0469 (2013.01);
(Continued)

(58) Field of Classification Search
CPC ............ A61B 17/0401; A61B 17/0469; A61B 17/06166; A61B 2017/00663;
(Continued)

(56) References Cited

U.S. PATENT DOCUMENTS 3,580,256 A 5/1971 Wilkinson
4,605,414 A 8/1986 Czajka
(Continued)

FOREIGN PATENT DOCUMENTS

CN 101252887 A 8/2008
CN 101888810 A 11/2010
(Continued)

OTHER PUBLICATIONS

Office Action from related Chinese Application No. 201380066543.7 dated Sep. 27, 2016.
(Continued)

Primary Examiner — Todd J Scherbel
(74) Attorney, Agent, or Firm — Burns & Levinson, LLP; Joseph M. Maraia

(57) ABSTRACT

An apparatus includes a flexible fixation member having a body with a longitudinal extent and a width, the body defining a plurality of openings through the body, each of the plurality of openings formed substantially cross wise through the width of the body, and a suture having two terminal ends, the suture being interwoven through each of the plurality of openings in the body of the fixation member such that multiple portions of the fixation member are slidably coupled to the suture and configurable to form a cluster within a surgical site.

7 Claims, 8 Drawing Sheets

Related U.S. Application Data continuation of application No. 14/304,269, filed on Jun. 13, 2014, now Pat. No. 9,078,651, which is a division of application No. 13/016,389, filed on Jan. 28, 2011, now Pat. No. 8,795,334.

(52) U.S. Cl.
CPC ...... *A61B 17/0482* (2013.01); *A61B 17/0487* (2013.01); *A61B 17/06166* (2013.01); *A61B 2017/00663* (2013.01); *A61B 2017/042* (2013.01); *A61B 2017/0409* (2013.01); *A61B 2017/0414* (2013.01); *A61B 2017/0459* (2013.01); *A61B 2017/0464* (2013.01)

(58) Field of Classification Search
CPC .... A61B 2017/0406; A61B 2017/0409; A61B 2017/0414; A61B 2017/0459; A61B 2017/0464; A61B 2017/0477; A61B 2017/0496; A61F 2/0811; A61F 2002/0852; A61F 2002/0882; A61F 2002/0888

See application file for complete search history.

(56) References Cited

U.S. PATENT DOCUMENTS

| | | | |
|---|---|---|---|
| 5,217,470 A | 6/1993 | Weston | |
| 5,234,445 A | 8/1993 | Walker et al. | |
| 5,306,301 A | 4/1994 | Graf et al. | |
| 5,405,352 A | 4/1995 | Weston | |
| 5,449,367 A | 9/1995 | Kadry | |
| 5,451,203 A | 9/1995 | Lamb | |
| 5,527,341 A | 6/1996 | Gogolewski et al. | |
| 5,645,588 A | 7/1997 | Graf et al. | |
| 5,690,649 A | 11/1997 | Li | |
| 5,718,717 A | 2/1998 | Bonutti | |
| 5,769,894 A | 6/1998 | Ferragamo | |
| 5,893,592 A | 4/1999 | Schulze et al. | |
| 5,919,232 A | 7/1999 | Chaffringeon et al. | |
| 5,989,252 A | 11/1999 | Fumex | |
| 5,993,459 A | 11/1999 | Larsen et al. | |
| 6,143,029 A | 11/2000 | Rippstein | |
| 6,193,754 B1 | 2/2001 | Seedhom | |
| 6,296,659 B1 | 10/2001 | Foerster | |
| 6,517,578 B2 | 2/2003 | Hein | |
| 7,048,754 B2 * | 5/2006 | Martin ................ | A61B 17/0469 606/228 |
| 7,390,329 B2 | 6/2008 | Westra et al. | |
| 7,390,332 B2 | 6/2008 | Selvitelli et al. | |
| 7,601,165 B2 | 10/2009 | Stone | |
| 7,658,751 B2 | 2/2010 | Stone | |
| 7,736,378 B2 | 6/2010 | Maahs et al. | |
| 7,749,250 B2 | 7/2010 | Stone et al. | |
| 7,771,455 B2 | 8/2010 | Ken | |
| 7,905,904 B2 | 3/2011 | Stone et al. | |
| 7,909,851 B2 | 3/2011 | Stone et al. | |
| 7,905,903 B2 | 5/2011 | Stone et al. | |
| 7,959,650 B2 | 6/2011 | Kaiser et al. | |
| 7,972,292 B2 | 7/2011 | Behl et al. | |
| 8,057,511 B2 | 11/2011 | Flores et al. | |
| 8,088,130 B2 | 1/2012 | Kaiser et al. | |
| 8,118,836 B2 | 2/2012 | Denham et al. | |
| 8,128,640 B2 | 3/2012 | Harris et al. | |
| 8,128,658 B2 | 3/2012 | Kaiser et al. | |
| 8,137,382 B2 | 3/2012 | Denham et al. | |
| 8,172,871 B2 | 5/2012 | Ken | |
| 8,241,305 B2 | 8/2012 | Stone | |
| 8,298,262 B2 | 10/2012 | Stone et al. | |
| 8,303,604 B2 | 11/2012 | Stone et al. | |
| 8,308,765 B2 | 11/2012 | Saadat et al. | |
| 8,361,113 B2 | 1/2013 | Stone et al. | |
| 8,409,253 B2 | 4/2013 | Stone et al. | |
| 8,795,334 B2 * | 8/2014 | Astorino ............ | A61B 17/0057 606/232 |
| 9,078,651 B2 * | 7/2015 | Astorino ............ | A61B 17/0057 |
| 9,370,352 B2 * | 6/2016 | Astorino ............ | A61B 17/0057 |
| 2001/0002440 A1 | 5/2001 | Bonutti | |
| 2001/0041938 A1 | 11/2001 | Hein | |
| 2002/0029066 A1 | 3/2002 | Foerster | |
| 2002/0115999 A1 | 8/2002 | McDevitt et al. | |
| 2003/0050666 A1 | 3/2003 | Grafton | |
| 2003/0130694 A1 | 7/2003 | Bojarski et al. | |
| 2003/0149448 A1 | 8/2003 | Foerster et al. | |
| 2004/0133238 A1 | 7/2004 | Cerier | |
| 2004/0181234 A1 | 9/2004 | McDevitt et al. | |
| 2004/0220573 A1 | 11/2004 | McDevitt et al. | |
| 2005/0033364 A1 | 2/2005 | Gregoire et al. | |
| 2005/0149118 A1 | 7/2005 | Koyfman et al. | |
| 2005/0187577 A1 | 8/2005 | Selvitelli et al. | |
| 2005/0209622 A1 | 9/2005 | Carrison | |
| 2005/0251159 A1 | 11/2005 | Ewers et al. | |
| 2005/0277985 A1 | 12/2005 | Wert et al. | |
| 2006/0155328 A1 | 7/2006 | Foerster | |
| 2006/0178680 A1 | 8/2006 | Nelson et al. | |
| 2006/0229671 A1 | 10/2006 | Steiner et al. | |
| 2006/0259076 A1 | 11/2006 | Burkhart et al. | |
| 2006/0293709 A1 | 12/2006 | Bojarski et al. | |
| 2007/0010857 A1 | 1/2007 | Sugimoto et al. | |
| 2007/0016244 A1 | 1/2007 | Behl et al. | |
| 2007/0156174 A1 | 7/2007 | Kaiser et al. | |
| 2007/0185532 A1 | 8/2007 | Stone et al. | |
| 2007/0239209 A1 | 10/2007 | Fallman | |
| 2008/0065114 A1 | 3/2008 | Stone et al. | |
| 2008/0140092 A1 | 6/2008 | Stone et al. | |
| 2008/0140093 A1 | 6/2008 | Stone et al. | |
| 2008/0188893 A1 | 8/2008 | Selvitelli et al. | |
| 2008/0208204 A1 | 8/2008 | Schmieding et al. | |
| 2008/0208252 A1 | 8/2008 | Holmes | |
| 2008/0255557 A1 | 10/2008 | Koyfman et al. | |
| 2008/0255613 A1 | 10/2008 | Kaiser et al. | |
| 2008/0312689 A1 | 12/2008 | Denham et al. | |
| 2009/0036905 A1 | 2/2009 | Schmieding | |
| 2009/0062846 A1 | 3/2009 | Ken | |
| 2009/0062847 A1 | 3/2009 | Ken | |
| 2009/0069823 A1 | 3/2009 | Foerster et al. | |
| 2009/0082805 A1 | 3/2009 | Kaiser et al. | |
| 2009/0240335 A1 | 9/2009 | Arcenio et al. | |
| 2009/0248068 A1 | 10/2009 | Lombardo et al. | |
| 2009/0259260 A1 | 10/2009 | Bentley et al. | |
| 2009/0306711 A1 | 12/2009 | Stone et al. | |
| 2009/0312776 A1 | 12/2009 | Kaiser et al. | |
| 2009/0318961 A1 | 12/2009 | Stone et al. | |
| 2010/0023056 A1 | 1/2010 | Johansson et al. | |
| 2010/0114163 A1 | 5/2010 | Martin | |
| 2010/0130989 A1 | 5/2010 | Bourque et al. | |
| 2010/0145384 A1 | 6/2010 | Stone et al. | |
| 2010/0211075 A1 | 8/2010 | Stone | |
| 2010/0249809 A1 | 9/2010 | Singhatat et al. | |
| 2010/0256677 A1 | 10/2010 | Albertorio et al. | |
| 2010/0268273 A1 | 10/2010 | Albertorio et al. | |
| 2010/0268275 A1 | 10/2010 | Stone et al. | |
| 2011/0009867 A1 | 1/2011 | Oren et al. | |
| 2011/0022061 A1 | 1/2011 | Orphanos et al. | |
| 2011/0022083 A1 | 1/2011 | DiMatteo et al. | |
| 2011/0022084 A1 | 1/2011 | Sengun et al. | |
| 2011/0077667 A1 | 3/2011 | Singhatat et al. | |
| 2011/0098727 A1 | 4/2011 | Kaiser et al. | |
| 2011/0098728 A1 | 4/2011 | McDevitt et al. | |
| 2011/0152885 A1 | 6/2011 | McDevitt et al. | |
| 2011/0152929 A1 | 6/2011 | McDevitt et al. | |
| 2011/0238111 A1 | 9/2011 | Frank | |
| 2011/0264141 A1 | 10/2011 | Denham et al. | |
| 2011/0270278 A1 | 11/2011 | Overes et al. | |
| 2012/0046693 A1 | 2/2012 | Denham et al. | |
| 2012/0053630 A1 | 3/2012 | Denham et al. | |
| 2012/0059417 A1 | 3/2012 | Norton et al. | |
| 2012/0116450 A1 | 5/2012 | McDevitt et al. | |
| 2012/0130422 A1 | 5/2012 | Hootstein | |
| 2012/0150297 A1 | 6/2012 | Denham et al. | |
| 2012/0197271 A1 | 8/2012 | Astorino et al. | |
| 2012/0215257 A1 | 8/2012 | Mcdevitt et al. | |
| 2012/0239085 A1 | 9/2012 | Schlotterback et al. | |
| 2012/0290004 A1 | 11/2012 | Lombardo et al. | |

(56) References Cited

U.S. PATENT DOCUMENTS

| | | |
|---|---|---|
| 2013/0018416 A1 | 1/2013 | Lombardo et al. |
| 2013/0023930 A1 | 1/2013 | Stone et al. |
| 2013/0035722 A1 | 2/2013 | McDevitt et al. |
| 2013/0110165 A1 | 5/2013 | Burkhart et al. |
| 2013/0123810 A1 | 5/2013 | Brown et al. |
| 2013/0123813 A1 | 5/2013 | Stone et al. |
| 2013/0138123 A1 | 5/2013 | Stone et al. |
| 2013/0158601 A1 | 6/2013 | Stone et al. |
| 2013/0237997 A1 | 9/2013 | Arai et al. |
| 2013/0296934 A1 | 11/2013 | Sengun |
| 2014/0114330 A1 | 4/2014 | Karasic et al. |

FOREIGN PATENT DOCUMENTS

| | | | |
|---|---|---|---|
| EP | 328401 | A1 | 8/1989 |
| EP | 2277456 | A1 | 1/2011 |
| FR | 2743294 | A1 | 7/1997 |
| GB | 2370227 | A | 6/2002 |
| JP | H08052155 | | 2/1996 |
| JP | 2006-503655 | A | 2/2006 |
| JP | 2010-500912 | A | 1/2010 |
| JP | 2010537746 | | 12/2010 |
| JP | 2011-025036 | A | 2/2011 |
| WO | 2003092551 | A1 | 11/2003 |
| WO | 2004037094 | A2 | 5/2004 |
| WO | 2007005394 | A1 | 1/2007 |
| WO | 2007/037326 | A1 | 4/2007 |
| WO | 2006086275 | A3 | 11/2007 |
| WO | 2008/022250 | A2 | 2/2008 |
| WO | 2009029914 | A1 | 3/2009 |
| WO | 2011058340 | A1 | 5/2011 |
| WO | 2012048050 | A1 | 4/2012 |
| WO | 2012103536 | A1 | 8/2012 |
| WO | 2012112793 | A1 | 8/2012 |
| WO | 2013134277 | A1 | 9/2013 |
| WO | 2014062684 | A1 | 4/2014 |

OTHER PUBLICATIONS

Office Action from related European Application No. 13712402.0-1654 dated Nov. 4, 2016.

Decision of Rejection from related Japanese Application No. 2013-551405 dated Jul. 25, 2016.

First Office Action from related Chinese Application No. 201380013146.3 dated Apr. 14, 2016.

Translation of Search Report from related Chinese Application No. 201380013146.3 dated May 26, 2016.

Office Communication from related European Application No. 13786021.9-1654 dated Dec. 13, 2016.

Patent Examination Report from related Australian Application No. 2013230095 dated Nov. 2, 2016.

"Shoulder Restoration System: Y-KnotTM 1.3mm All-Suture Anchor," ConMedTM Linvatec, 2011, 4 pages.

"Shoulder Restoration System: Arthroscopic Bankart Repair Using the Y-KnotTM 1.3mm All-Suture Anchor," ConMedTM Linvatec, 2011, 4 pages.

International Search Report Application No. PCT/US2012/029143, dated Jun. 13, 2013.

International Search Report Application No. PCT/US2013/065064, dated Feb. 21, 2014.

Communication Pursuant to Article 94(3) EPC for European Application No. 12702737.3, dated Feb. 24, 2016.

Inquiry made in Course of Substantive Examination of Russian Application No. 2013138875/14(058923), mailed Nov. 18, 2015.

First Office Action for Chinese Application No. 201280006593.1, dated Sep. 2, 2015.

Communication of the Substantive Examination Report for Mexican Application No. MX/a/2013/008734, dated Jul. 27, 2015.

Patent Examination Report No. 1 for Australian Application No. 2012211072, dated Aug. 12, 2015.

"Technique for ACL reconstruction with Acufex Director Drill Guide and Endobutton CL" copyright 1999, Smith & Nephew, Inc., 20 pages.

"Endobutton Direct: Fixation Device," Smith & Nephew, Inc., reprinted from http:/fglobal.smith-nephew.com/us/product23376_5895.htm, on Nov. 22, 2010, 3 pages.

"Endobutton CL," Smith and Nephew, Inc., reprinted from http://fendo.smith-nephew.com/es/Standard.asp?NodeiD=2715, on Nov. 22, 2010, 1 page.

From, S. "ACL Reconstruction with Bone-Tendon-Bone Transplants using the Endobutton CL BTB Fixation System," Smith & Nephew, Inc., copyright 2004, printed on Apr. 4, 11 pages.

Scope This Out, vol. 10, No. 2, Summer 2008, 8 pages.

Scope This Out, vol. 12, No. 2, Fall 2010, 8 pages.

Scope this Out, vol. 12, No. 1, Spring 2010, 8 pages.

ToggleLOC: Femoral Fixation Device with Zip Loop Technology, Biomet Sports Medicine, Inc., 2007, 8 pages.

Glousman, R., et al., "JuggerKnot Soft Anchor Surgical Technique," Biomet Sports Medicine, 2010, 1 page.

Game Plan: Innovative Products to be Launched AAOS 2010, Biomet Sports Medicine, Spring 2010, vol. 2, No. 3, 1 page.

Lawhorn, K., "MaxFire MarXmen Device Surgical Technique," Biomet Sports Medicine, 2010, 1 page.

International Search Report for International Application No. PCT/US2012/023056, dated Jun. 13, 2012.

Written Opinion of the International Searching Authority and the and International Preliminary Report on Patentability D for International Application No. PCT/US2012/023056, dated Jun. 13, 2012.

Office Action from related Chinese Application No. 201380013146.3 dated Dec. 26, 2016.

Office Action from related Japanese Application No. 2014-561043 dated Jan. 16, 2017.

Office Action from related Russian Application No. 2014136769/14(059452) dated Dec. 30, 2017.

Office Action from related European Application No. 12702737.3-1664 dated Feb. 21, 2017.

Decision to Reject the Amendments in Japanese Patent Application 2016-228862 dated Apr. 11, 2018.

European Application No. 12702737.3-1122 Office Action.

Application No. 2016-228862—Pre-Appeal Report—Examiner's Comments dated Nov. 29, 2018.

European Application No. 12702737.3-1122 Examination Report dated Nov. 19, 2019.

Japanese Application No. 2016-228862 Notice of Reasons for Rejection dated Oct. 18, 2019.

Indian Examination Report Application No. 6029/DELNP/2013 dated Oct. 12, 2019.

* cited by examiner

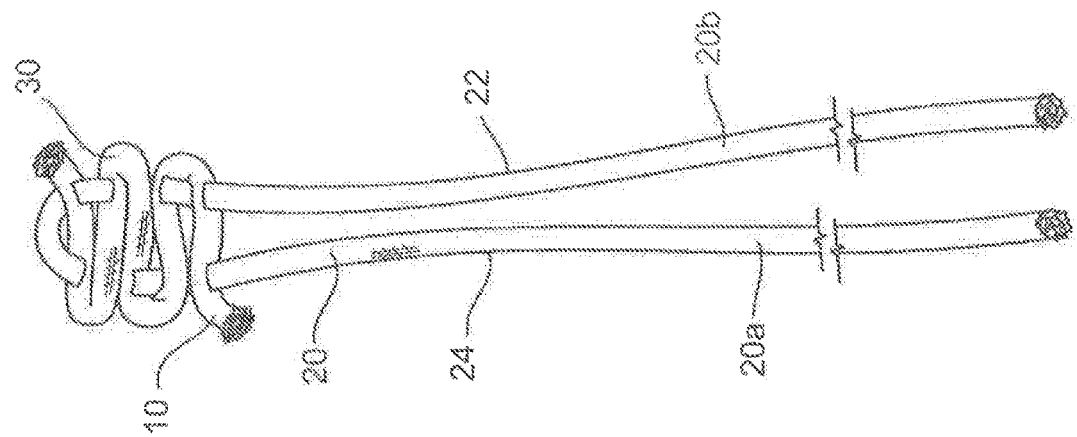
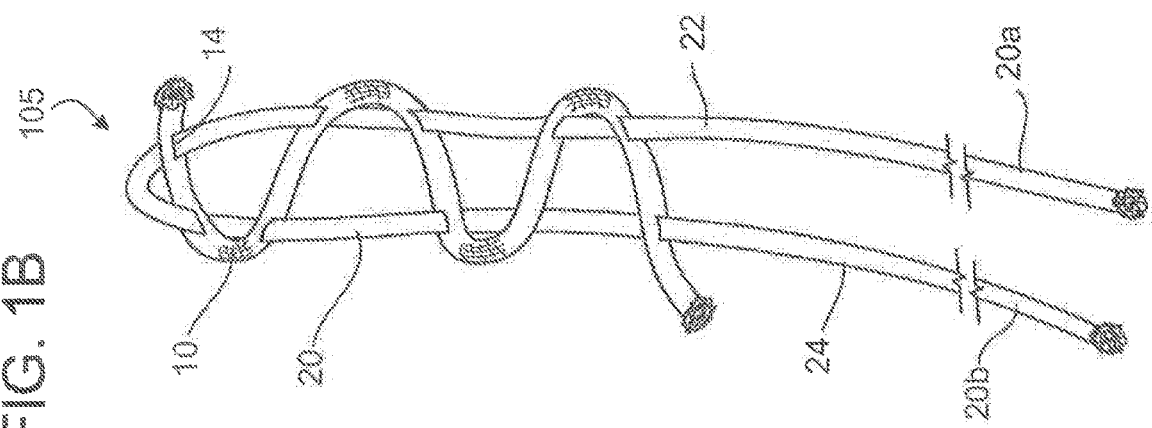
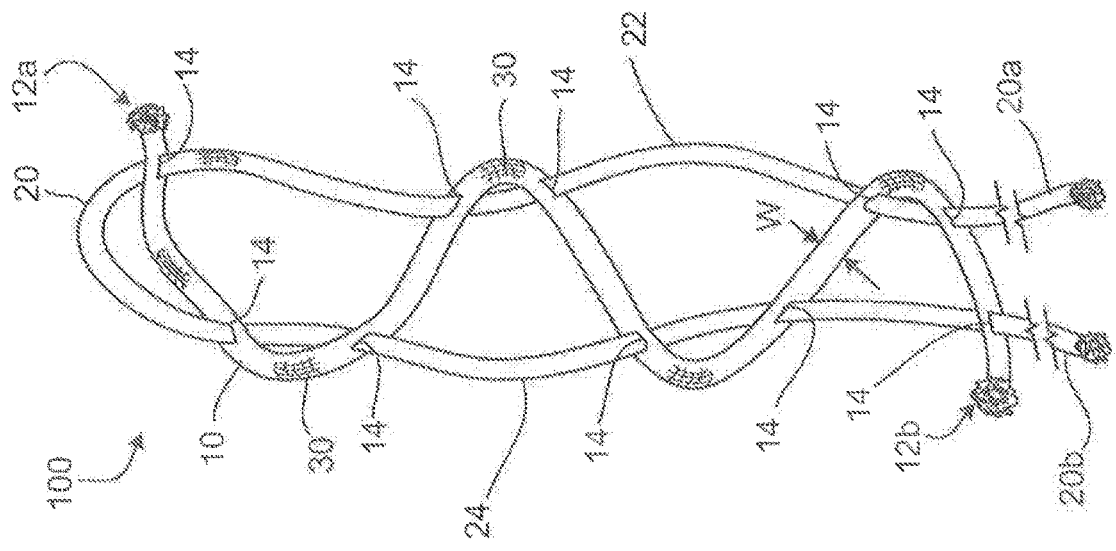

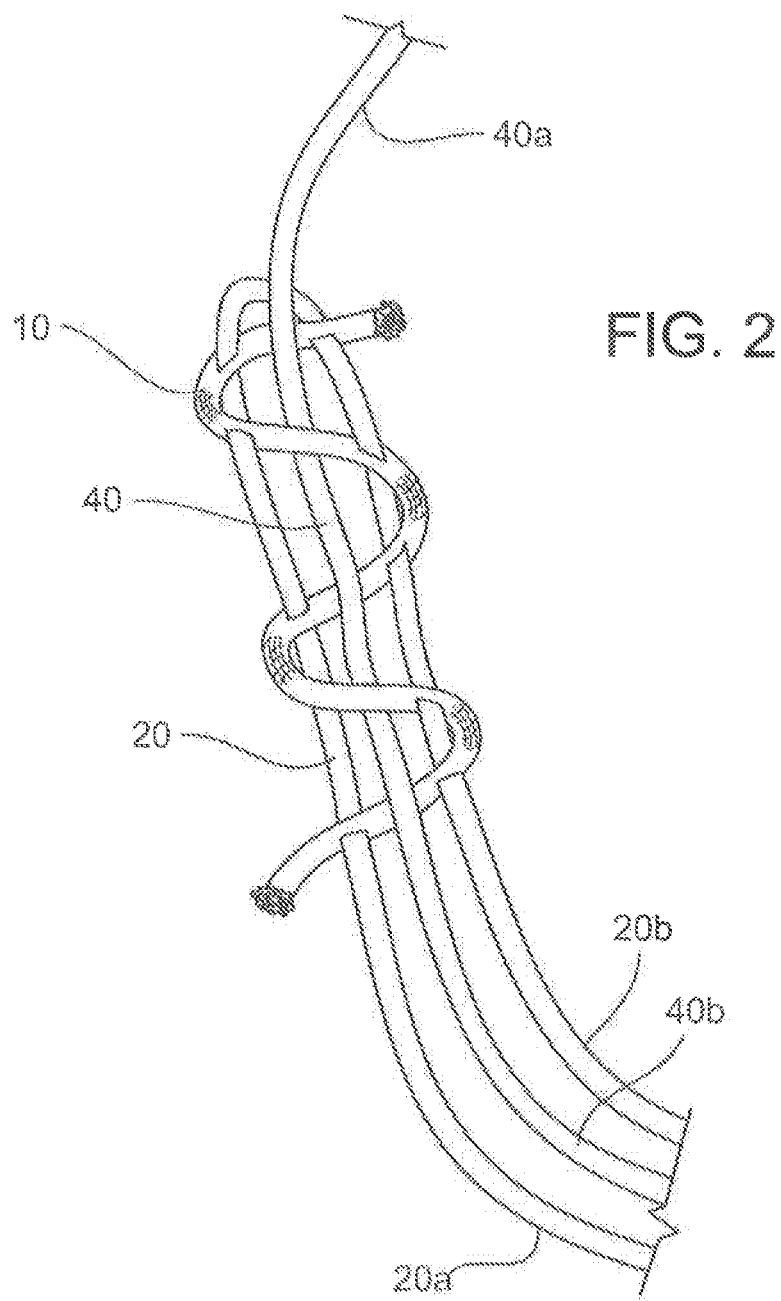

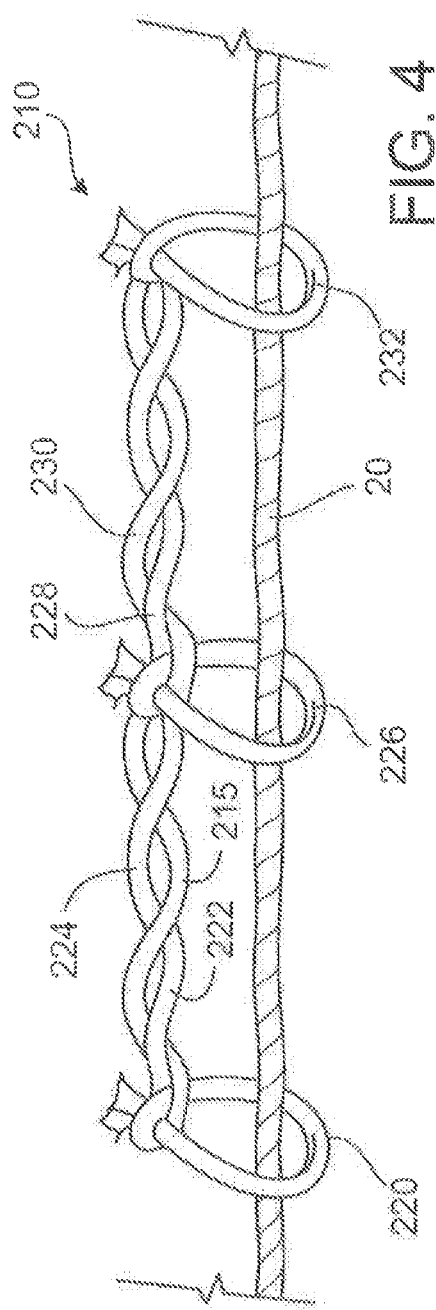
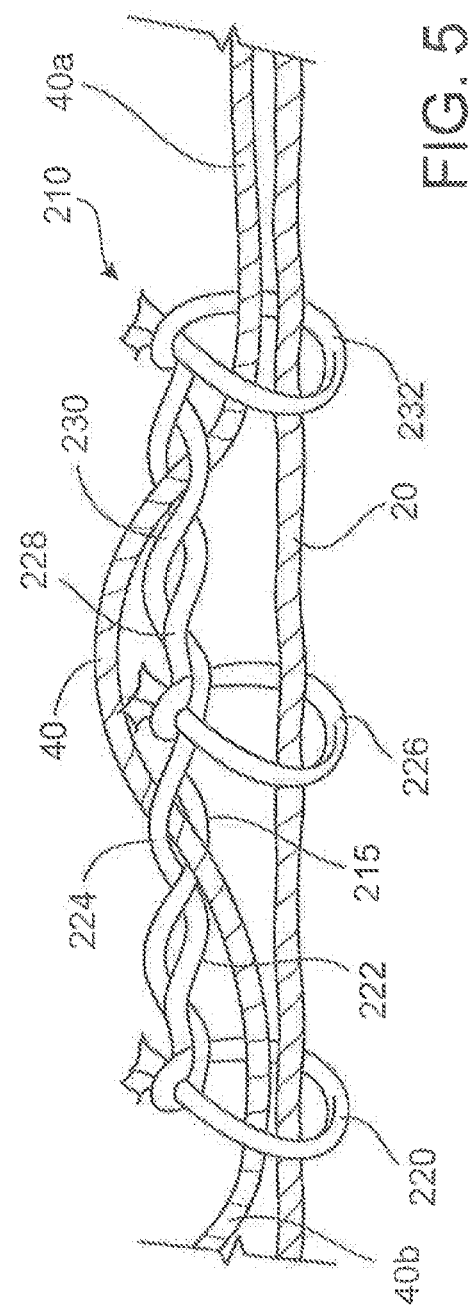

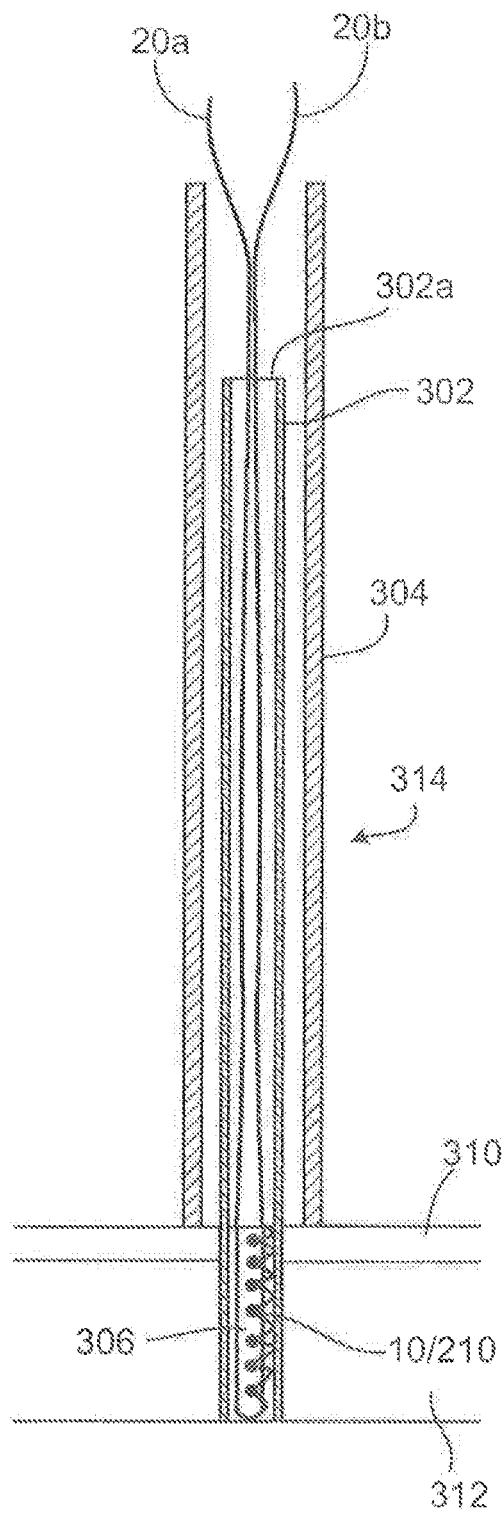
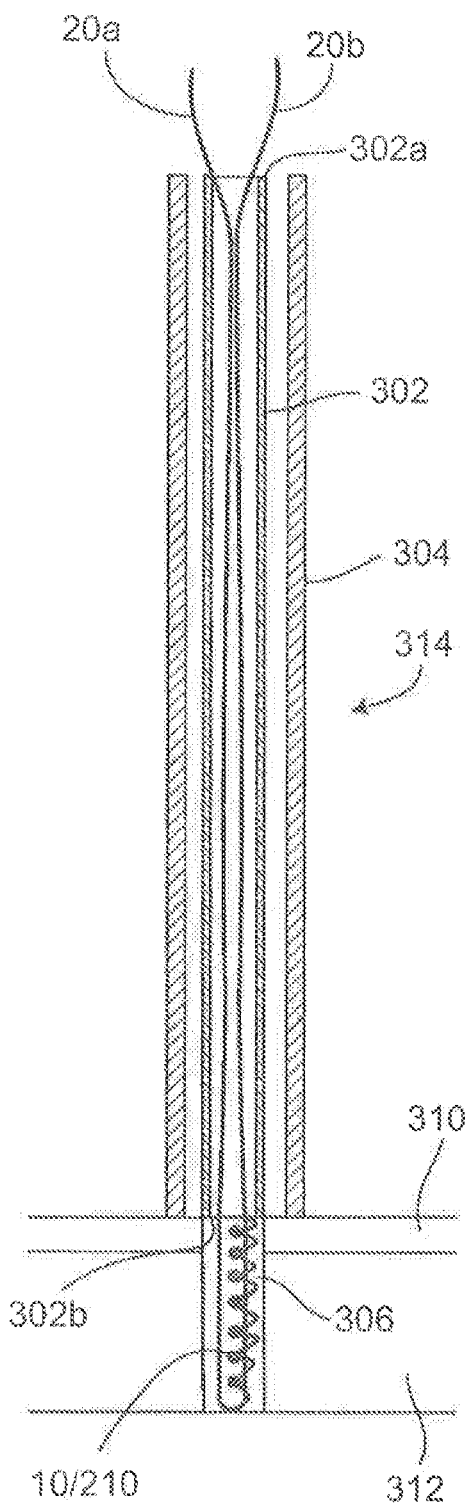
FIG. 6C
FIG. 6D

TISSUE REPAIR

CROSS-REFERENCE TO RELATED APPLICATION(S)

This application is a continuation of co-pending U.S. patent application Ser. No. 14/693,322, filed Apr. 22, 2015, entitled TISSUE REPAIR, which is a continuation of U.S. patent application Ser. No. 14/304,269, filed Jun. 13, 2014, now U.S. Pat. No. 9,078,651, issued Jul. 14, 2015, which is a divisional of U.S. patent application Ser. No. 13/016,389, filed on Jan. 28, 2011, now U.S. Pat. No. 8,795,334, issued Aug. 5, 2014. The entire contents of the prior applications are hereby incorporated herein by reference for all purposes.

TECHNICAL FIELD

This disclosure relates to apparatus and methods for repairing tissue, and more particularly, to apparatus and methods for coupling soft tissue to bone.

BACKGROUND

Arthroscopic procedures using sutures and suture anchors have been used in tissue repair to, for example, secure soft tissue to bone. Suture anchors, such as metallic or other absorbable or non-absorbable polymer materials, tend to displace a certain volume of hone to provide adequate fixation strength. The larger a necessary repair may require multiple anchors to properly reattach torn soft tissue to bone. The size of many of these anchors can limit the number and location of fixation points as well as affect the anatomic nature of some tissue repairs. Small anchors typically do not provide, sufficient holding strength to be effective in some tissue repair procedures or certain bone areas

SUMMARY

In one general aspect, an apparatus comprises a flexible fixation member comprising a body with a longitudinal extent and a width, the body defining a plurality of openings through the body, each of the plurality of openings formed substantially cross wise through the width of the body, and a suture comprising two terminal ends, the suture being interwoven through each of the plurality of openings in the body of the fixation member such that multiple portions of the fixation member are slidably coupled to the suture and configurable to form a cluster within a surgical site.

Implementations may include one or more of the following features. For example, the flexible fixation member comprises one of a suture, tape, braid, or mesh. The flexible fixation member is non-tubular. The flexible fixation member and the suture comprise a size 2 suture. The apparatus further comprises a delivery device comprising a cannula configured to receive the flexible fixation member therein. The delivery device further comprises an elongated member configured to slide within the cannula from a retracted position to an advanced position and configured to eject the flexible fixation member from the cannula when the elongated member is in the advanced position. The portions of the fixation member are configured to slide relative to the suture to form a cluster comprising a group of folds within a surgical site. The suture is interwoven through the plurality of openings in the fixation member to form two substantially parallel tail sections of suture. The fixation member comprises at least one curved portion that comprises, in series along the curved portion, a first opening receiving a portion of one of the two parallel tail sections, a second and third opening receiving portions of the other of the two parallel tail sections, and a fourth opening receiving another portion of the one of the two parallel tail sections. The fixation member and the suture are formed from a material that is absorbable within a body of a patient. The fixation member comprises a biologic growth material. In addition, the apparatus further comprises a second suture having two terminal ends, the second suture being interwoven through each of the plurality of openings in the body of the fixation member such that portions of the fixation member are slidably coupled to the suture.

In another general aspect, an assembly comprises a non-tubular tissue anchor formed from one of a suture, mesh, braid, or tape, the tissue anchor comprising a body with a longitudinal extent and a width, the body defining a plurality of openings along the longitudinal extent of the body and through the width of the body, a suture interwoven through each of the plurality of openings in the body of the tissue anchor such that portions of the tissue anchor are slidable relative to the suture and configurable to form a cluster within a surgical site, and a delivery device comprising a cannula configured to receive the flexible fixation member therein.

Implementations may include one or more of the following features. For example, the delivery device further comprises an elongated member configured to slide within the cannula from a retracted position to an advanced position and configured to eject the flexible fixation member from the cannula when the elongated member is in the advanced position. The tissue anchor and the suture comprise a size 2 suture. The portions of the tissue anchor are configured to slide relative to the suture to form a cluster comprising a group of folds within a surgical site. The suture is interwoven through each of the plurality of openings in the tissue anchor to form two substantially parallel tail sections of suture. The tissue anchor and the suture are formed from a material that is absorbable within a body of a patient. The tissue anchor comprises a biologic growth material.

In another general aspect, an apparatus comprises a tissue anchor comprising a plurality of connected knots, and a suture comprising two terminal ends, the suture passing through one or more of the plurality of connected knots such that the tissue anchor is slidably coupled to the suture.

Implementations may include one or more of the following features. For example, the plurality of connected knots comprise, in sequence, a first square knot, two free alternating post half hitch knots, a second square knot, two free alternating post half hitch knots, and a third square knot. The suture passes through each of the first, second, and third square knots. The apparatus further comprises a second suture having two terminal ends, the second suture passing through one or more of the plurality of connected knots such that the tissue anchor is slidably coupled to the second suture. The tissue anchor and the suture are formed from a material that is absorbable within a body of a patient. The tissue anchor comprises a biologic growth material. The apparatus further comprises a delivery device comprising a cannula configured to receive the tissue anchor therein. The delivery device further comprises an elongated member configured to slide within the cannula from a retracted position to an advanced position and configured to eject the tissue anchor from the cannula when the elongated member is in the advanced position.

In another general aspect, a wound closure assembly comprises a tissue anchor comprising a plurality of connected knots, and a suture comprising two terminal ends, the suture passing through one or more of the plurality of connected knots such that the tissue anchor is slidably coupled to the suture, and a delivery device comprising a cannula configured to receive the tissue anchor therein.

Implementations may include one or more of the following features. For example, the delivery device further comprises an elongated member configured to slide within the cannula from a retracted position to an advanced position and configured to eject the tissue anchor from the cannula when the elongated member is in the advanced position.

In another general aspect, a method of closing a tissue wound comprises delivering a wound closure device to a surgical site, the wound closure device comprising a flexible fixation member having a body with a longitudinal extent and a width, the body defining a plurality of openings through the body, each of the plurality of openings formed substantially cross wise through the width of the body, and a suture having two terminal ends, the suture being interwoven through each of the plurality of openings in the body of the fixation member such that multiple portions of the fixation member are slidably coupled to the suture and configurable to form a cluster within a surgical site, removing the flexible fixation member from the wound closure device at the surgical site, and pulling on the terminal ends of the suture to form a cluster of the multiple portions of the fixation member at the surgical site.

Implementations may include one or more of the following features. For example, the method further comprises drilling a hole into the tissue. The removing step comprises ejecting the flexible fixation member from the device into the hole. The hole passes completely through the tissue and the delivering stop comprises delivering the device through the hole and the removing step comprises placing the flexible fixation member on an opposite side of the hole. The method further comprises maintaining, the wound closure device in position at the surgical site as the terminal ends of the suture are pulled to form the cluster of the multiple portions of the fixation member at the surgical site.

In another general aspect, a method of closing a tissue wound, comprises delivering a wound closure device to a surgical site, the wound closure device comprising a tissue anchor having a plurality of connected knots, and a suture having two terminal ends, the suture passing through one or more of the plurality of connected knots such that the tissue anchor is slidably coupled to the suture, removing the tissue anchor from the wound closure device at the surgical site, and pulling on the terminal ends of the suture to form a cluster of the plurality of connected knots at the surgical site.

Implementations may include one or more of the following features. For example, the method further comprises drilling a hole into the tissue. The removing step comprises ejecting the tissue anchor from the device into the hole. The hole passes completely through the tissue and the delivering step comprises delivering the device through the hole and the removing step comprises placing the tissue anchor on an opposite side of the hole. The method further comprises maintaining the wound closure device in position at the surgical site as the terminal ends of the suture are pulled to form the cluster of the plurality of connected knots at the surgical site.

The details of one or more implementations of the disclosure are set forth in the accompanying drawings and the description below. Other features and advantages will be apparent from the description and drawings, and from the claims.

BRIEF DESCRIPTION OF THE DRAWINGS

FIG. 1A illustrates an implementation of a tissue repair apparatus.

FIG. 1B illustrates another implementation of a tissue repair apparatus.

FIG. 1C illustrates an implementation of a tissue repair apparatus after sliding of curved portions of a fixation member with respect to a suture to form a cluster or bunch including a number of folds.

FIG. 2 illustrates the tissue repair apparatus of FIG. 1A including an additional suture interwoven through the construct.

FIG. 4 illustrates another implementation of a tissue repair apparatus.

FIG. 5 illustrates the tissue repair apparatus of FIG. 4 including an additional suture interwoven through the construct.

FIGS. 6A-6G illustrate implementations of delivery devices used for delivery and placement of the tissue repair apparatuses of FIGS. 1A-5 at a surgical site.

DETAILED DESCRIPTION

Figure 3:
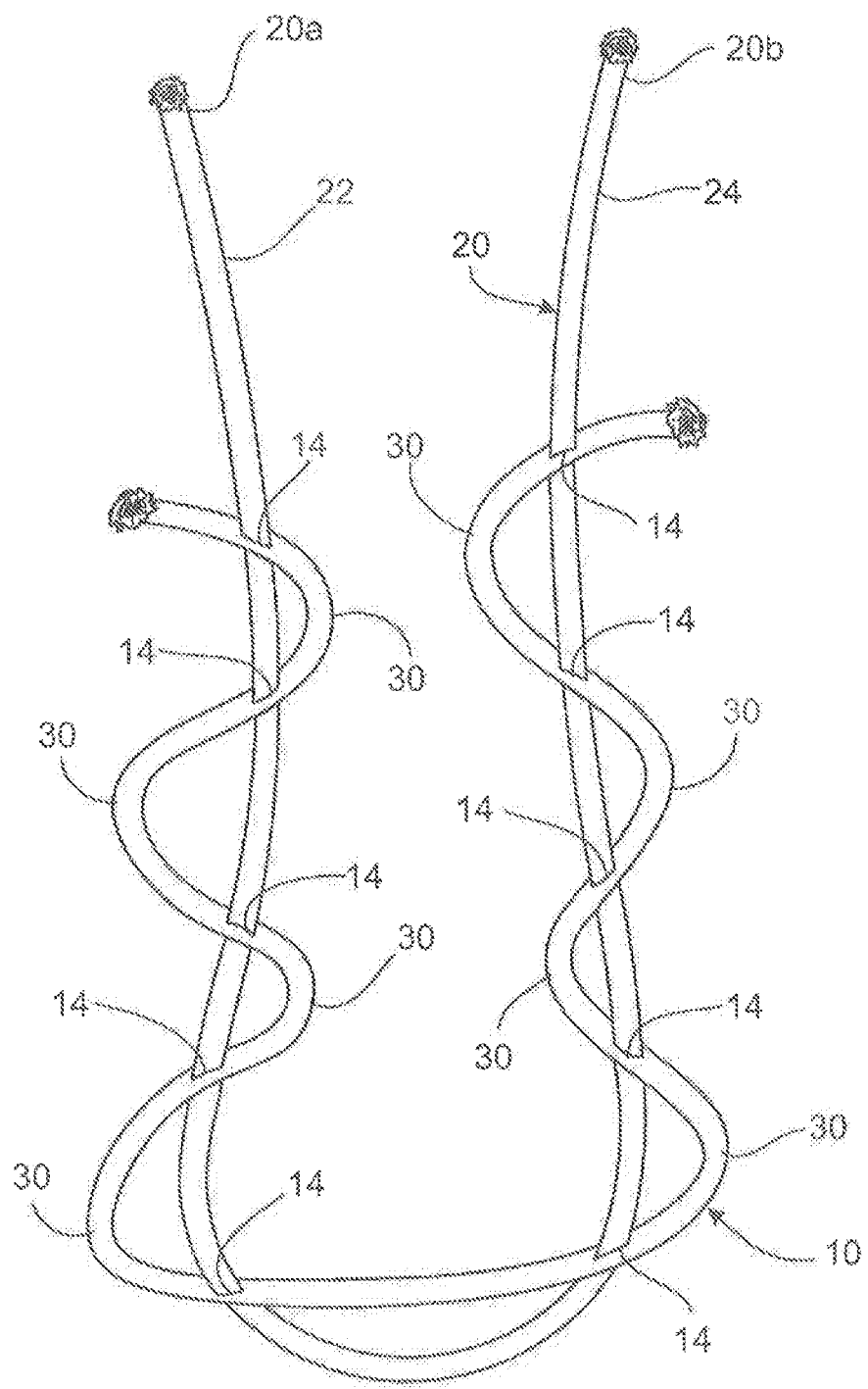
FIG. 3 illustrates an alternative implementation of weaving the suture through the fixation member of FIG. 1A.

Referring to FIG. 1A, a tissue repair apparatus 100 includes a fixation member or anchor 10 and a flexible member or suture 20 interwoven through the fixation member 10. The fixation member 10 is formed of a malleable or flexible braided body 12 having a longitudinal extent extending between a first end 12a and a second end 12b and a width W. The body 12 defines a plurality of openings 14 formed crosswise through, or substantially along, the width W of the body 12. The suture 20 includes two terminal ends, 20a and 20b. One of the terminal ends 20a, 20b is passed through each of the openings 14 in the body 12 forming multiple curved portions 30 of the fixation member 10 and two substantially parallel sections 22, 24 of the suture 20. As shown in FIG. 1A, the curved portions 30 pass from one section 22, 24 to the other of the sections 22, 24 along the length of the fixation member 10 to form substantially S-shaped curved portions 30. The curved portions 30 may slide with respect to the suture 20 to form a cluster or bunch 30 including a number of folds as shown in FIG. 1C. The cluster 30, in conjunction with the terminal ends 20a, 20b, may be used to secure tissue within a surgical site as will be described in more detail below.

In the implementation shown in FIG. 1A, the fixation member 10 and the suture 20 are made from size 2 non-tubular braided sutures. However, the fixation member 10 may be a tape, mesh, tube, or other type of malleable or flexible structure, and the suture 20 may be made from a suture of different size depending upon the surgical procedure or application. For example, in another exemplary implementation, the fixation member 10 and/or the suture 20 are made from a flattened tubular suture. In addition, while the fixation member 10 of FIG. 1A includes at least four curved portions 30, other configurations are possible, such as the implementation shown in FIG. 1B, where the fixation member 10 has a smaller length dimension and therefore includes three curved portions 30 when the suture 20 is interwoven therethrough. In yet another implementation, the fixation member 10 can include two curved portions 30 and be formed substantially in a S-shaped configuration. Varying the length and width dimensions of the fixation member 10, and/or varying the size of the suture 20, and/or the number of openings through the fixation member 10 through which the suture 20 passes, may affect the size of the cluster 30 formed by the fixation member 10 within the surgical site.

These varying configurations may provide the user with flexibility to meet the needs for a number of various surgical procedures.

Referring to FIG. 2, the tissue repair apparatus 100 of FIG. 1A may also include an additional flexible member or suture 40 having two terminal ends 40a, 40b. One of the two ends 40a, 40b may be interwoven around or through the fixation member 20 forming a construct yielding four free ends 20a, 20b, 40a, and 40b. An apparatus with four free ends may have advantages over two free ends in certain implementations. For example, in some applications, such as rotator cuff repair, it is often necessary to tie down the tissue to the bone at two locations in order to secure the tissue to the bone. In these applications, providing four free ends with only one fixation member within the bone reduces the number of fixation members needed, which may lower procedure time and cost. Reducing the number of fixation members may also reduce the risk of stress concentrations due to multiple drilled holes causing a risk of fracture at the repair site post-operatively.

Referring to FIG. 3, an alternative implementation of weaving the suture 20 through the fixation member 10 of FIG. 1A is illustrated. One of the terminal ends 20a, 20b is passed through each of the openings 14 in the body 12 forming multiple curved portions 30 of the fixation member 10 and two substantially parallel sections 22, 24 of the suture 20. Unlike the curved portions 30 formed by the weaving pattern illustrated in FIG. 1A, the curved portions 30 of FIG. 3 do not pass from one tail section 22, 24 to the other of the tail sections 22, 24 along the length of the fixation member 10 to form substantially S-shaped curved portions 30. Instead, in the implementation shown in FIG. 3, curved portions 30 form substantially S-shaped curved portions 30 along the length of the portion of the suture 10 that is interwoven through the fixation member 10. This weaving pattern may allow for a smaller diameter hole to be drilled into bone for receiving the fixation member 10, which may aid in the reduction of stress concentrations and fracture. In addition, the weaving pattern may permit access to surgical sites that are too small or confined for existing tissue anchor assemblies.

Referring to FIG. 4, in another implementation, an apparatus for tissue repair 200 includes a fixation member or anchor 210 and the flexible member or suture 20 interwoven through the fixation member 210. The fixation member 210 may be formed as a sequence of connected knots 215. In the particular implementation shown in FIG. 4, the sequence of knots 215 includes a square knot 220, two free alternating post half hitch knots 222, 224, a square knot 226, two free alternating post half hitch knots 228, 230, and a square knot 232. The suture 20 may pass through each of the square knots 220, 226, and 232, or any combination of one or more openings formed by the connected knots 215 that permits the fixation member 210 to slide relative to the suture 20 so that the fixation member 210 may form a cluster or bunch within the surgical site and cooperate with the suture 20 to secure tissue within the surgical site as will be described in more detail below. The fixation member 210 and the suture 20 are made from size 2 braided sutures, however, other suture sizes may be employed or tailored for, for example, drill size and strength requirements.

Referring to FIG. 5, the tissue repair apparatus 200 of FIG. 4 may also include an additional flexible member or suture 40 having two terminal ends 40a, 40b. One of the two ends 40a, 40b may be interwoven around or through the fixation member 210, and more particularly, through one or more openings formed by the sequence of knots 215, forming a construct yielding four free ends 20a, 20b, 40a, and 40b. As discussed above, an apparatus with four free ends may have advantages over two free ends in various implementations.

Figure 6A:
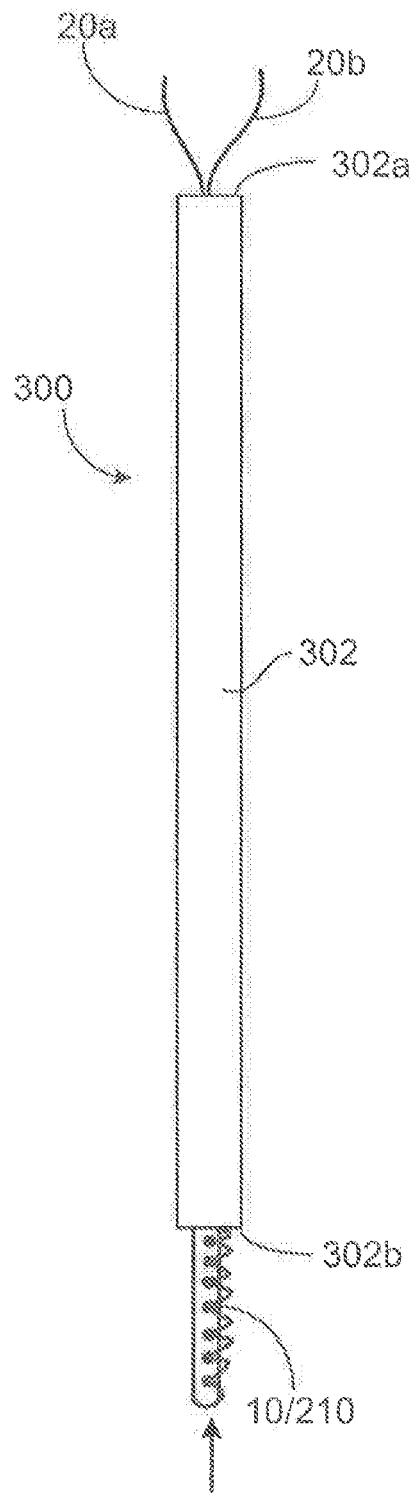
Figure 6B:
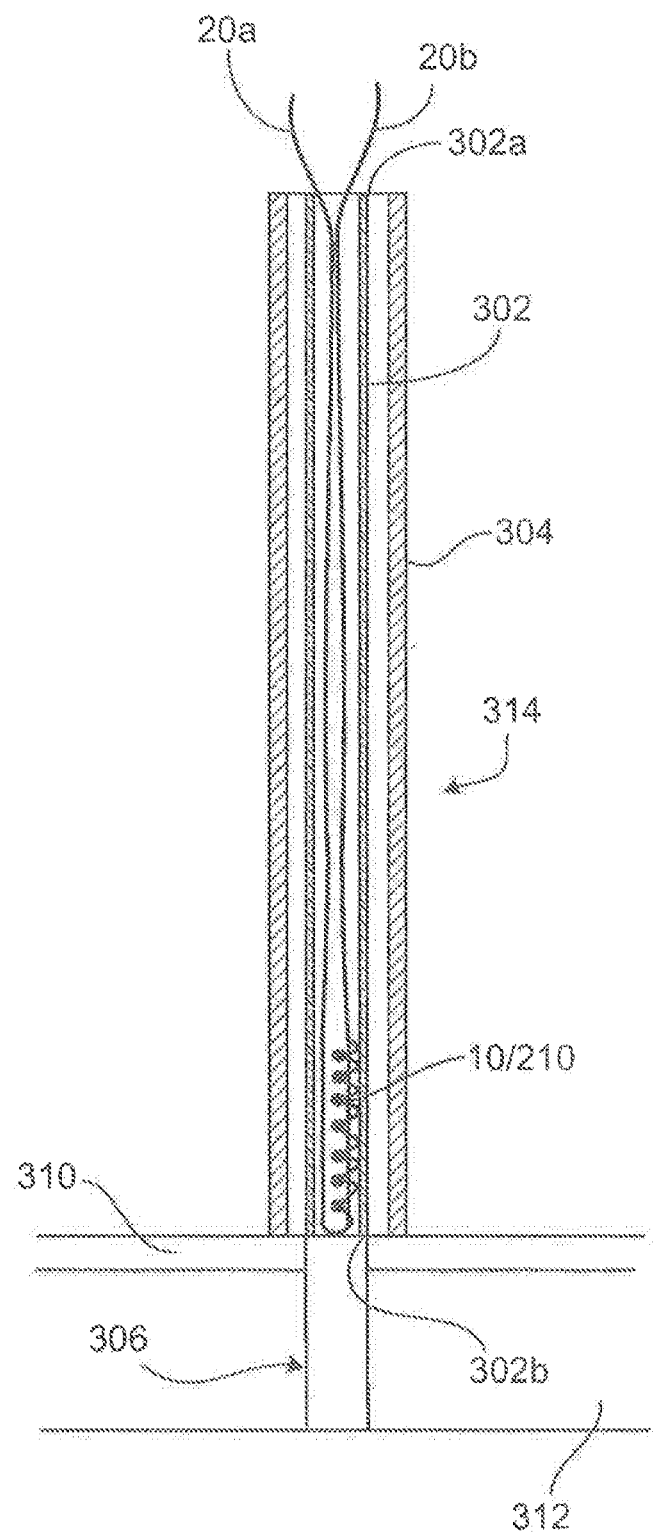

FIGS. 6A-6E represent a tool or delivery device 300 used to deliver any one of the fixation members 10, 210 described with respect to FIGS. 1A, 1B, and 2-3 to a surgical site for repairing, as an example, soft tissue 314. Referring to FIG. 6A, the delivery device 300 includes an inserter tube or cannula 302. One of the fixation members 10, 210 is loaded into the tube or cannula 302 as shown by the arrow in FIG. 6A such that the free ends 20a, 20b of the suture 20 extend through a proximal end 302a of the inserter tube 302 such that the free ends 20a, 20b may be manipulated by a physician. As shown in FIG. 6B, a drill guide 304 is placed within the surgical site 400 and a drill (not shown) is placed within the drill guide 304 and is used to drill a hole 306 of sufficient depth through the cortical layer 310 and into the cancellous bone tissue 312. Alternatively, the drill may be used to drill completely through the cancellous bone tissue 312 in the ease of transosseous repair applications. Once the hole 306 is formed in the surgical site 400, the inserter tube 302 containing the loaded fixation member 10, 210 is inserted through the drill guide 304 and into a desired position at the surgical site 400, for example, the inserter tube 302 is tapped into the cortical layer 310.

Referring to FIG. 6C, the inserter tube 302 may then be moved or tapped further into the hole 306 with the fixation member 10, 210 remaining in position within the inserter tube 302. Once the tube 302 is in the desired position within the hole 306, the user may then draw the inserter tube 302 back leaving the fixation member 10, 210 within, the hole 306 in the bone (FIG. 6D), or alternatively, on an opposite side of the bone in a transosseous application.

Figure 6E:
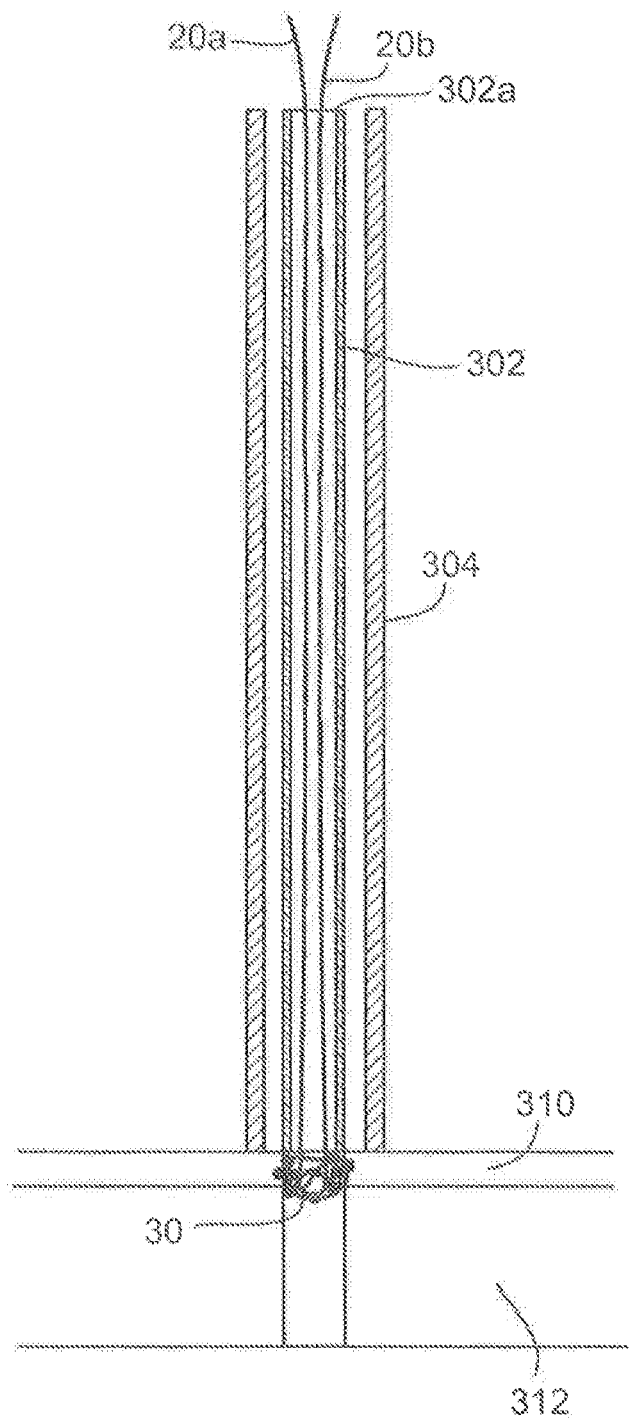

Referring to FIG. 6E, with the fixation member 10, 210 positioned within the hole 306 and a distal end 302b of the inserter tube 302 positioned at the surgical site 400, for example, at or below the cortical layer 310, the user may then pull on one or both of the free ends 20a, 20b of the suture 20. Pulling one or both of the free ends 20a, 20b (and/or the free ends 40a, 40b in those implementations employing two sutures, such as sutures 20, 40 shown in FIG. 2) causes the fixation member 10, 210 to seat against the distal end 302b of the inserter tube 302. As the user continues to pull one or both of the free ends 20a, 20b, the fixation member 10, 210 slides relative to the suture 20, and more particularly, the curved portions 30 of the fixation member 10, or the sequence of knots 215 of the fixation member 210, slide relative to the suture 20 to come together to form a bunch or cluster 30 within the hole 306, for example, at or below the cortical layer 310. With the fixation member 10, 210 in the desired position, the user may then remove the inserter tube 302 and drill guide 304 from the surgical site 400 and tie the free ends 20a, 20b (and/or the free ends 40a, 40b) to secure the tissue 314 to the bone 312.

Maintaining the inserter tube 302 in place throughout insertion and deployment of the fixation member 10, 210 into the surgical site 400 may provide the user with tactile feedback that the fixation member 10, 210 is seated against the inserter tube 302. This may be advantageous over procedures that rely instead on the cortical layer 310 to provide a hard-stop against deployment of the fixation member 10, 210 within the surgical site 400. In those systems, the user feels a fixation member seat or deploy once it contacts the cortical layer 310, which is of various densities across patients. Therefore, the cortical layer 310 in some patients may feel like a hard stop, and in some patients may feel like a soft stop. Thus, there is an increased risk of pulling the fixation member out when trying to deploy or seat the fixation member when relying on the cortical layer to provide a stop to fixation member deployment. In contrast, in the present implementation, the user is provided with a tactile feedback through the inserter tube 302 that the fixation member 10, 210 has deployed and has formed the requisite bunch or cluster within the surgical site 400. This helps reduce the risk of pulling the fixation member 10, 210 out when deploying and seating the fixation member 10, 210.

A number of implementations of the invention have been described. Nevertheless, it will be understood that various modifications may be made without departing from the spirit and scope of the invention. For example, the fixation members and the flexible members may include a growth factor, such as, for example, an angiogenic factor. The fixation members and the flexible members may also be loaded with a bioactive material, a stimulant, or any substance that promotes healing of the tissue. In addition, while the openings formed in the body of the fixation member are described as being formed substantially crosswise through the body, they may be formed in other orientations depending on the particular application. Moreover, the openings may be formed in the body of the fixation member prior to passing the flexible member through the openings, or the opening may be formed by passing the flexible member through the body of the fixation member, such as, for example, by passing a needle loaded with the flexible member through the body of the fixation member to form a desired number of openings in the fixation member.

Figure 6F:
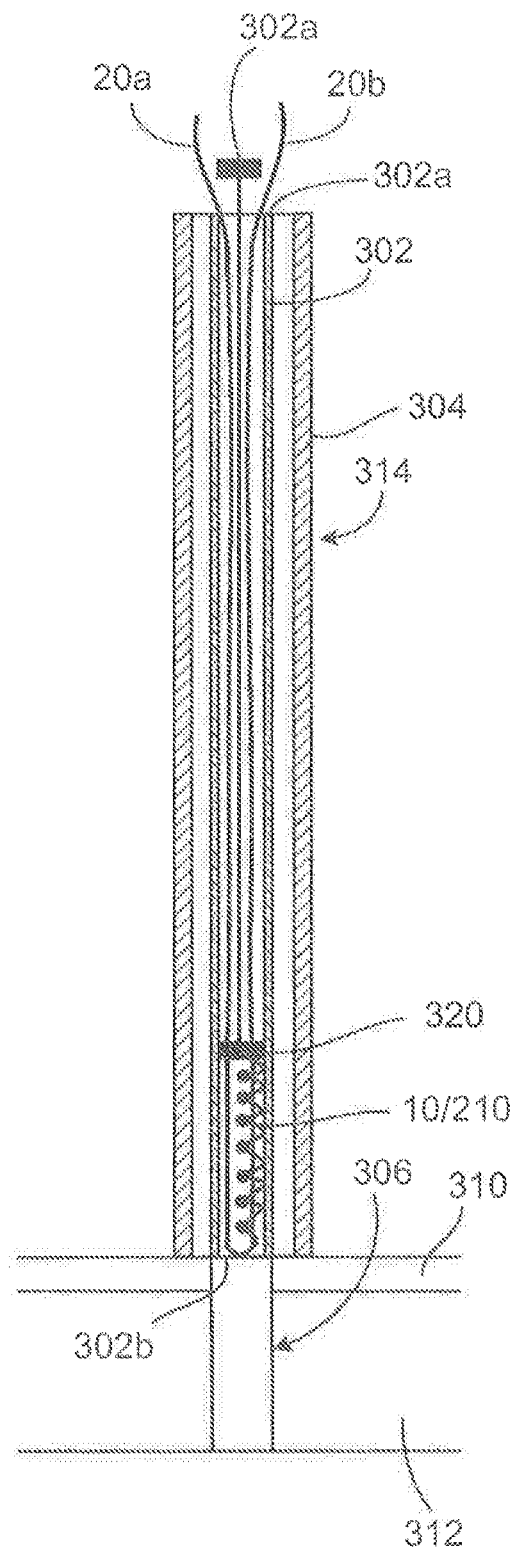
Figure 6G:
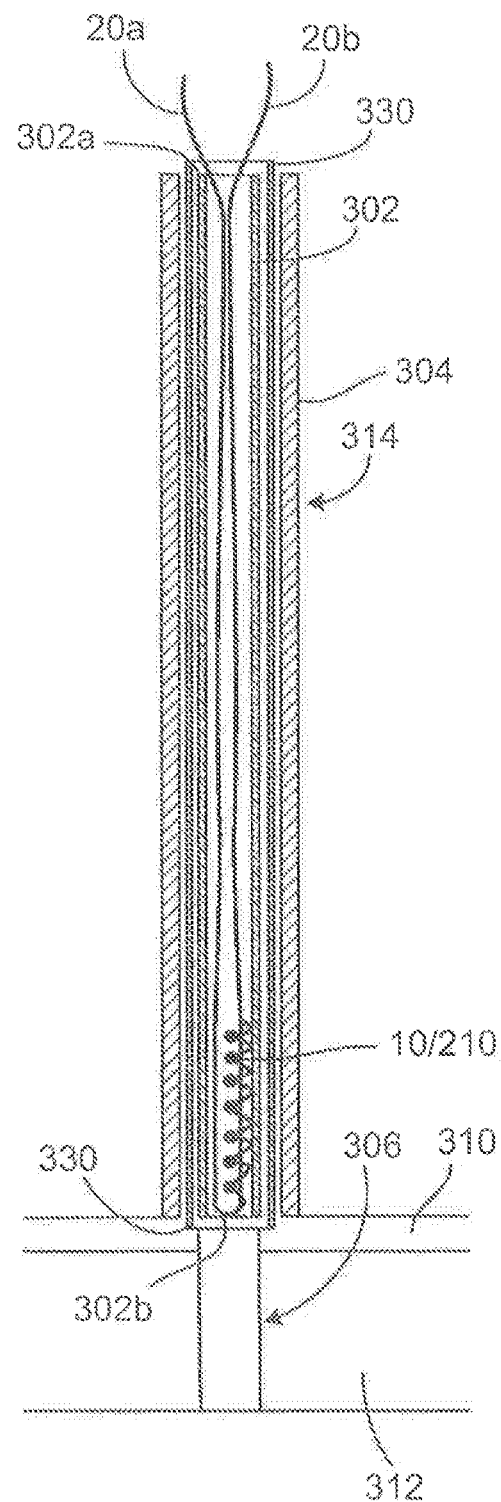

In addition, although the process has been described for applications where the fixation member is secured within a hole drilled into bone, the fixation members may also be used in transosseous applications where the depth of the hole is not a constraint. In these applications, the fixation member may be passed entirely through the hole and secured on the backside of the bone. In an alternative implementation (FIG. 6F), the inserter tube 302 may be maintained on top of the cortical layer 310 throughout insertion of the fixation member 10, 210 into the hole 306. In such an implementation, the delivery device 300 includes a slide member 320 disposed within the inserter tube 302 and coupled to the fixation member 10, 210. The user may move the slide member 320 forward within the inserter tube 302 to deploy the fixation member 10, 210 from the inserter tube 302 and into the hole 306. In yet another alternative implementation (FIG. 6G), the delivery device 300 may include a tube 330 placed through the drill guide 304. The tube 330 is tapped into the cortical layer 310 and then receives the inserter tube 302 therethrough. In addition, although the delivery device 300, including the inserter tube 302, has been shown with a straight configuration, the delivery device 300, including the inserter tube 302, may have a curved shape or other suitable configuration depending on the particular surgical location and procedure to be performed.

Moreover, in addition to the particular knot sequence described with respect to the fixation member 210 of FIG. 4, it should be understood that various knot sequences and sizes, and suture sizes, may be used depending on the particular application. Accordingly, other implementations are within the scope of the following claims.

What is claimed is:

1. An apparatus for insertion into a bone hole comprising:
   a flexible fixation member comprising a single, unitary body formed by first and second legs and a U-shaped bend joining the first and second legs, each of the first and second legs terminating in a free end, the U-shaped bend having an apex, and wherein the apex of the U-shaped bend does not define an opening; and
   a non-looped suture strand passing through the fixation member along a length of the body between the free ends of the body such that portions of the fixation member are slidable relative to the suture strand, the suture strand having first and second end regions, the first end region extending freely from an opening in the first leg of the body without passing through the second leg, and the second end region extending freely from an opening in the second leg of the body without passing through the first leg, the suture strand extending along the U-shaped bend of the fixation member in a single direction without intersecting itself;
   wherein the suture strand does not include a knot formed from the suture strand; and
   wherein, upon tensioning the suture strand, the fixation member is configured to form an anchor within the bone hole.

2. The apparatus of claim 1, wherein the fixation member comprises suture, tape, braid or mesh.

3. The apparatus of claim 1, wherein the suture strand extends longitudinally down the first leg of the fixation member and longitudinally up the second leg of the fixation member.

4. The apparatus of claim 1, wherein the first end region of the suture strand only extends a single time through the opening in the first leg and wherein the second end region of the suture strand only extends a single time through the opening in the second leg.

5. The apparatus of claim 1, wherein the anchor is defined by a cluster comprising a group of folds within the bone hole.

6. An assembly comprising:
   an apparatus comprising:
      a flexible fixation member comprising a single, unitary body formed by first and second legs and a U-shaped bend joining the first and second legs, each of the first and second legs terminating in a free end, the U-shaped bend having an apex and wherein the apex of the U-shaped bend does not define an opening; and
      a non-looped suture strand passing through the fixation member along a length of the body between the free ends of the body such that portions of the fixation member are slidable relative to the suture strand, the suture strand having first and second end regions, the first end region extending freely from an opening in the first leg of the body without passing through the second leg, and the second end region extending freely from an opening in the second leg of the body without passing through the first leg, the suture strand extending along the U-shaped bend of the fixation member in a single direction without intersecting itself;
      wherein the suture strand does not include a knot formed from the suture strand; and
      wherein, upon tensioning the suture strand, the fixation member is configured to form an anchor within the bone hole; and
   a delivery device.

7. The assembly of claim 6, wherein the delivery device comprises an elongated member configured to slide from a retracted position to an advanced position within the bone hole, and wherein the U-shaped bend of the fixation member is positioned toward a distal end of the elongated member.

\* \* \* \* \*